United States Patent
Hartwig et al.

(10) Patent No.: US 10,010,511 B2
(45) Date of Patent: Jul. 3, 2018

(54) TRANSDERMAL DRUG DELIVERY SYSTEM

(71) Applicant: ProSolus, Inc., San Antonio, TX (US)

(72) Inventors: Rod L. Hartwig, Cooper City, FL (US); David Houze, Coral Gables, FL (US)

(73) Assignee: ProSolus, Inc., San Antonio, TX (US)

( * ) Notice: Subject to any disclaimer, the term of this patent is extended or adjusted under 35 U.S.C. 154(b) by 71 days.

(21) Appl. No.: 15/163,737

(22) Filed: May 25, 2016

(65) Prior Publication Data

US 2017/0340577 A1    Nov. 30, 2017

(51) Int. Cl.
*A61K 9/70* (2006.01)
*A61K 31/4168* (2006.01)
*A61K 47/02* (2006.01)
*A61M 35/00* (2006.01)

(52) U.S. Cl.
CPC ........ *A61K 9/7053* (2013.01); *A61K 31/4168* (2013.01); *A61K 47/02* (2013.01); *A61M 35/00* (2013.01)

(58) Field of Classification Search
CPC .................................................. A61M 35/00
See application file for complete search history.

(56) References Cited

U.S. PATENT DOCUMENTS

| | | | |
|---|---|---|---|
| 5,676,968 A | 10/1997 | Lipp et al. | |
| 9,408,802 B1 * | 8/2016 | Hartwig | A61K 9/0014 |
| 2006/0078604 A1 | 4/2006 | Kanios et al. | |
| 2010/0178323 A1 | 7/2010 | Kydonieus et al. | |
| 2011/0054043 A1 | 3/2011 | Funaki et al. | |
| 2015/0238436 A1 * | 8/2015 | Urushihara | A61K 9/7061 604/307 |
| 2017/0246111 A1 * | 8/2017 | Monsuur | A61K 9/143 |

FOREIGN PATENT DOCUMENTS

JP    WO 2014046243 A1 *  3/2014  ........... A61K 9/7061

* cited by examiner

*Primary Examiner* — Gina C Justice
(74) *Attorney, Agent, or Firm* — Dority & Manning, P.A.

(57) ABSTRACT

A transdermal drug delivery system is provided that includes a drug-in-adhesive matrix layer and a backing layer. The matrix layer includes an active pharmaceutical ingredient, a cross-linked polyvinylpyrrolidone binder, a mesoporous silicon dioxide filler, and a pressure sensitive adhesive, while the backing layer forms an exterior facing-surface of the delivery system. The ratio of the mesoporous silicon dioxide filler to the cross-linked polyvinylpyrrolidone binder ranges from about 1:1 to about 1:8. As a result of the specific components of the matrix layer and the amounts in which they are utilized, the resulting delivery system, which can include a homogeneous dispersion of the active pharmaceutical ingredient in the formulation, is capable of delivering the active pharmaceutical ingredient over a period of up to about 7 days in a generally constant and controlled fashion. Further, the only layer that contemplates the use of an adhesive component is the drug-in-adhesive matrix layer.

20 Claims, 4 Drawing Sheets

TRANSDERMAL DRUG DELIVERY SYSTEM

BACKGROUND OF THE INVENTION

Transdermal drug delivery systems are used to deliver an active pharmaceutical ingredient (API) or drug to a patient over an extended time period, typically from a period of hours up to about 7 days. Over the years, various types of transdermal drug delivery systems or patches have entered the market, including reservoir-type systems and monolithic matrix-type systems. Reservoir type systems are those that contain a drug reservoir embedded between an impervious backing layer and a rate controlling membrane or additional layers of adhesives, where the drug is in the form of a solution, a suspension, a gel, or drug-in-adhesive (DIA) matrix. Reservoir systems use a skin-contacting adhesive which is applied to the skin-facing surface of the system so the patch can be adhered to a patient's skin. Monolithic DIA systems, on the other hand, are systems in which the drug is contained within an adhesive matrix that functions as both the adhesive layer for securing the patch to the skin and the drug-containing layer. The DIA layer is protected with an impervious backing or film on a surface of the matrix opposite the skin-contacting surface. However, a problem with monolithic DIA transdermal systems is that the diffusion of the drug through the skin of the patient and into the bloodstream is often initially high and exhibits a rapid decrease over time so that the drug delivery is not controlled at the desired rate. Such a phenomenon is known as depletion and can lead to initial over-dosing of a drug or under-dosing of a drug at the end of the patch's application period, where neither is beneficial to the patient.

In consideration of the aforementioned problem, a need exists for a transdermal drug delivery system where the rate of delivery of the drug is controlled so that the delivery is generally constant over an extended period of time.

SUMMARY OF THE INVENTION

In accordance with one embodiment of the present invention, a transdermal drug delivery system is disclosed. The transdermal drug delivery system includes drug-in-adhesive matrix layer that includes an active pharmaceutical ingredient, a cross-linked polyvinylpyrrolidone binder, a mesoporous silicon dioxide filler, and a pressure sensitive adhesive; and a backing layer, where the backing layer forms an exterior facing-surface of the transdermal drug delivery system. The ratio of the mesoporous silicon dioxide filler to the cross-linked polyvinylpyrrolidone binder ranges from about 1:1 to about 1:8.

In one particular embodiment of the present invention, the mesoporous silicon dioxide filler has a pH ranging from about 6 to about 8.

In one more embodiment of the present invention, the mesoporous silicon dioxide filler can be in the form of particles having an average particle size ranging from about 1 micrometer to about 10 micrometers. Further, the particles can have an average pore size ranging from about 2 nanometers to about 50 nanometers.

In an additional embodiment of the present invention, the cross-linked polyvinylpyrrolidone binder can be in the form of particles having an average particle size ranging from about 1 micrometers to about 40 micrometers. In still another embodiment of the present invention, the cross-linked polyvinylpyrrolidone binder can be in the form of particles having a bulk density ranging from about 0.10 g/mL to about 0.4 g/mL.

In yet another embodiment of the present invention, the cross-linked polyvinylpyrrolidone binder can be in the form of particles having a surface area ranging from about 0.5 $m^2/g$ to about 20 $m^2/g$.

In an additional embodiment of the present invention, the pressure sensitive adhesive can include polyisobutylene.

In one more embodiment of the present invention, the active pharmaceutical ingredient can be clonidine. Further, the clonidine can be present in the transdermal drug delivery system at a concentration ranging from about 0.2 $mg/cm^2$ to about 1 $mg/cm^2$.

In another embodiment of the present invention, the drug-in-adhesive matrix layer can further include an oil-based plasticizer.

In an additional embodiment of the present invention, the transdermal delivery system can also include a release liner, where the release liner can be disposed on a skin-contacting surface of the drug-in-adhesive matrix layer. In one more embodiment of the present invention, the active pharmaceutical ingredient is delivered to a patient at a generally constant rate for up to about 7 days. Further, the active pharmaceutical ingredient can be homogeneously distributed throughout the drug-in-adhesive matrix layer, wherein the drug-in-adhesive matrix layer is the only adhesive-containing component in the transdermal drug delivery system.

The present invention also contemplates a method of providing transdermal delivery of an active pharmaceutical ingredient to a patient for up to about seven days. The method includes providing the transdermal delivery system as discussed above; affixing the transdermal delivery system to the patient; and transdermally delivering the active pharmaceutical ingredient to the patient. In accordance with another embodiment of the present invention, a method of making a drug-in-adhesive matrix layer for a transdermal drug delivery system is disclosed. The method includes providing an active pharmaceutical ingredient; adding a cross-linked polyvinylpyrrolidone binder to the active pharmaceutical ingredient to form a blend; adding a polar solvent to the blend; adding a pressure sensitive adhesive dissolved in a non-polar solvent to the blend; adding a plasticizer to the blend; and adding a mesoporous silicon dioxide filler to the blend such that the ratio of the mesoporous silicon dioxide filler to the cross-linked polyvinylpyrrolidone binder ranges from about 1:1 to about 1:8.

In one more embodiment of the method contemplated by the present invention, the mesoporous silicon dioxide filler can have a pH ranging from about 6 to about 8. In yet another embodiment of the method contemplated by the present invention, the mesoporous silicon dioxide filler is in the form of particles having an average particle size ranging from about 1 micrometer to about 10 micrometers. In an additional embodiment of the method contemplated by the present invention, the cross-linked polyvinylpyrrolidone binder is in the form of particles having an average particle size ranging from about 1 micrometer to about 40 micrometers.

In still another embodiment of the method contemplated by the present invention, the polar solvent can be ethyl acetate and the non-polar solvent can be heptane.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figure, in which.

Figure 1:
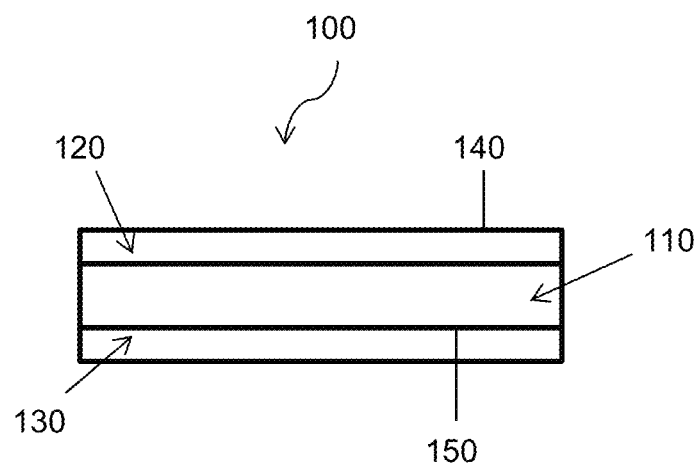
FIG. 1 is a cross-sectional view of a transdermal drug delivery system according to one embodiment of the present disclosure.

Repeat use of reference characters in the present specification and drawing is intended to represent the same or analogous features or elements of the present invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention.

Generally speaking, the present invention is directed to a transdermal drug delivery system. Referring to FIG. 1 and according to one particular embodiment, the transdermal drug delivery system 100 includes a drug-in-adhesive matrix layer 110 disposed between a backing layer 120 and a release liner 130. The backing layer 120 has an exterior surface 140 that is exposed to the ambient environment when the transdermal drug delivery system 100 is in use. Meanwhile, the release liner 130 is positioned on a skin-contacting surface 150 of the drug-in-adhesive matrix layer 110, where the release liner 130 is removable so that the drug-in-adhesive matrix layer 110 can be positioned directly on the skin during use of the transdermal drug delivery system 100. As a result of the specific combination of components and their weight percentages, such as, inter alia, the ratio of the particular silicon dioxide filler and binder utilized, the present inventors have found that the transdermal drug delivery system 100 can include a homogeneous drug-in-adhesive matrix layer that forms a skin-contacting surface, which facilitates the delivery of the drug (i.e., active pharmaceutical ingredient or API) in a controlled manner over a time period of up to about 7 days, where the only adhesive layer utilized is the drug-in-adhesive matrix layer that comes into direct contact with a patient's skin during use. In other words, the drug-in-adhesive matrix 110 is the only adhesive-containing component in the transdermal drug delivery system. As shown in FIG. 1, the drug-in-adhesive matrix layer 110 can be in the form of a single layer so that the active pharmaceutical ingredient is homogeneously dispersed throughout adhesive component of the device 100, unlike prior art devices that require a drug or API reservoir layer in conjunction with at least one separate adhesive layer that forms the skin contacting surface, where such prior art devices thus contemplate a heterogeneous distribution of the drug or API due to the presence of at least one additional adhesive layer.

Figure 7:
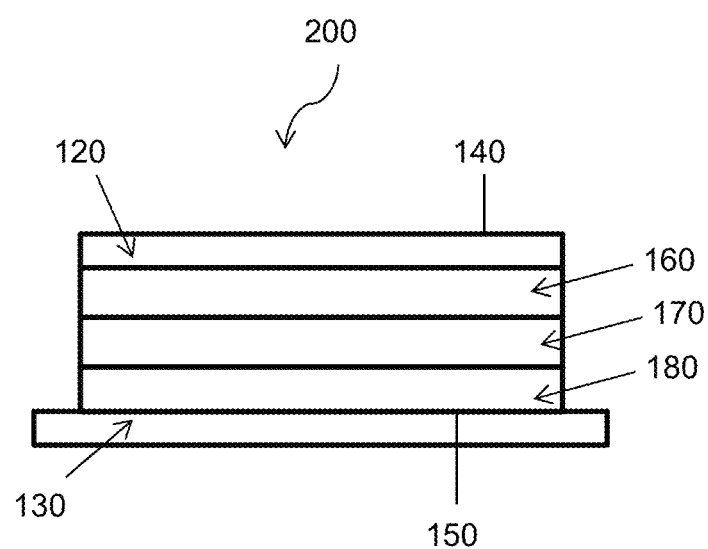
FIG. 7 is a cross-sectional view of a transdermal drug delivery system according to the prior art (specifically, Catapres® TTS).

For example, referring to FIG. 7, one transdermal drug delivery system described by the prior art is the Catapres® TTS device 200 which requires an active pharmaceutical ingredient reservoir 160 disposed between a backing layer 120 and a control membrane 170, where a separate adhesive layer 180 is disposed between the control membrane 170 and a release liner 130. The backing layer 120 has an exterior surface 140 that is exposed to the ambient environment when the transdermal drug delivery system 200 is in use. Meanwhile, the release liner 130 is positioned on a skin-contacting surface 150 of the adhesive layer 180, where the release liner 130 is removable so that the adhesive layer 180 can be positioned directly on the skin during use of the prior art transdermal drug delivery system 200. Still other prior art devices (not shown), require a backing layer, a solid matrix reservoir containing the API, a separate adhesive layer, and a release liner (e.g., Mylan Pharmaceuticals Inc.'s clonidine patch); a backing layer, a drug reservoir layer, an ethylene vinyl acetate membrane for delivery control, a silicone adhesive layer, an acrylate adhesive layer, and a release liner (e.g., Par Pharmaceutical, Inc.'s clonidine patch); a backing layer, a drug reservoir, a polypropylene membrane, an adhesive layer, and a release liner (e.g., Teva Pharmaceuticals Industries, Ltd.'s clonidine patch). Thus, the aforementioned devices all require at least one adhesive layer that is separate from the drug-in-adhesive matrix layer, such that none of the aforementioned devices contemplate a monolithic drug-in-adhesive matrix layer that facilitates a homogeneous dispersion of the API in the adhesive for controlled delivery of the API when the drug-in-adhesive matrix layer is in direct contact with a patient's skin.

The various components of the transdermal drug delivery system 100 are discussed in detail below.

I. Drug-in-Adhesive Matrix Layer Polymer Blend a. Active Pharmaceutical Ingredient The polymer blend use to form the drug-in-adhesive matrix layer of the transdermal drug delivery system of the present invention can include any suitable drug or active pharmaceutical ingredient (API). In one particular embodiment, the API can be clonidine. Clonidine is a medication used to treat high blood pressure, attention deficit hyperactivity disorder, anxiety disorders, withdrawal (from either alcohol, opioids, or smoking), migraine headaches, menopausal flushing, diarrhea, and certain pain conditions. It is classified as a centrally acting α2 adrenergic agonist and an imidazoline receptor agonist.

In another particular embodiment, the API can be guanfacine. Guanfacine is a medication used to treat high blood pressure and attention deficit hyperactivity disorder. Guanfacine is a selective $\alpha_{2A}$ receptor agonist.

In still another particular embodiment, the API can be rotigotine. Rotigotine is a non-dihydroergotoxine D3/D2/D1 dopamine receptor agonist, and research shows that it has therapeutic effects on a variety of central nervous system diseases and mental disorders. Rotigotine can be prescribed for the treatment or mitigation of Parkinson's disease, Restless Legs Syndrome, schizophrenia, and depression and can also be prescribed for the preventive treatment of Parkinson's disease.

Regardless of the particular API utilized, the amount of the API contained in a polymer blend used to form the drug-in-adhesive matrix layer can range from about 0.5 wt. % to about 10 wt. %, such as from about 0.75 wt. % to about 5 wt. %, such as from about 1 wt. % to about 2.5 wt. % based on the wet weight of the polymer blend. Meanwhile, after the polymer blend is coated onto, for instance, a backing layer and then dried to form the drug-in-adhesive matrix layer, the API can be present in an amount ranging, from about 1 wt. % to about 20 wt. %, such as from about 2 wt. % to about 15 wt. %, such as from about 3 wt. % to about 10 wt. % based on the dry weight of the drug-in-adhesive matrix layer after the transdermal drug delivery system is assembled and ready for use.

b. Binder

The drug-in-adhesive matrix layer of the transdermal drug delivery system of the present invention can also include a binder that is a cross-linked polyvinylpyrrolidone (PVP), such as a cross-linked homopolymer of N-vinyl-2-pyrrolidone. In one particular embodiment, the cross-linked PVP is in the form of a water-insoluble powder. Such cross-linked PVPs are commercially available under the name Kollidon®, available from BASF. A specific example of a cross-linked PVP that is contemplated for use in the present invention is Kollidon® CL-M. Other cross-linked PVPs that can be used include Kollidon® CL-SF and CL-F. The cross-linked PVP can be micronized and can have an average particle size ranging from about 1 micrometer to about 40 micrometers, such as from about 2 micrometers to about 30 micrometers, such as from about 3 micrometers to about 10 micrometers. In addition, in one particular embodiment, greater than 90% of the particles utilized can have a particle size less than about 15 micrometers. The particle size of the cross-linked PVP contemplated for use in the drug-in-adhesive matrix layer of the present invention is thus smaller than typical cross-linked PVPs, which can have particle sizes up to 150 micrometers. Without intending to be limited by any particular theory, the present inventors have found that utilizing a cross-linked PVP where greater than 90% of the particles have a particle size less than about 15 micrometers can result in the formation of a stable polymer blend that is used to form the drug-in-adhesive matrix layer, where the API is maintained in a uniform suspension with minimal sedimentation. This, in turn, enables the formation of a homogeneous dispersion of the API in the matrix so that the transdermal drug delivery system can deliver the API in a controlled manner for up to about 7 days without an excessive burst of drug permeation initially that unacceptably tapers off over time.

Moreover, the cross-linked PVP particles contemplated for use in the present invention can have a bulk density ranging from about 0.10 g/mL to about 0.40 g/mL, such as from about 0.125 g/mL to about 0.35 g/mL, such as from about 0.15 g/mL to about 0.25 g/mL. Further, the cross-linked PVP particles can have a surface area ranging from about 0.5 $m^2/g$ to about 20 $m^2/g$, such as from about 1 $m^2/g$ to about 15 $m^2/g$, such as from about 1.5 $m^2/g$ to about 10 $m^2/g$. The increased surface area of the cross-linked PVP particles contemplated for use in the present invention can facilitate the dispersion of the API in a uniform, homogeneous manner throughout the drug-in-adhesive matrix layer, which enables the API to be delivered at a constant rate.

The amount of the binder contained in a polymer blend used to form the drug-in-adhesive matrix layer can range from about 0.5 wt. % to about 10 wt. %, such as from about 0.75 wt. % to about 5 wt. %, such as from about 1 wt. % to about 2.5 wt. % based on the wet weight of the polymer blend. Meanwhile, after the polymer blend is coated onto, for instance, a backing layer and then dried to form the drug-in-adhesive matrix layer, the binder can be present in an amount ranging from about 1 wt. % to about 15 wt. %, such as from about 1.5 wt. % to about 12.5 wt. %, such as from about 2 wt. % to about 10 wt. % based on the dry weight of the drug-in-adhesive matrix layer after the transdermal drug delivery system is assembled and ready for use.

c. Polar Solvent

The polymer blend from which drug-in-adhesive matrix layer of the transdermal drug delivery system of the present invention is formed can include any suitable polar solvent effective to facilitate dissolution of the API in the drug-in-adhesive matrix layer. In one particular embodiment, the polar solvent can be ethyl acetate. Other polar solvents that can be used include ethanol, methanol, isopropanol, and water.

Regardless of the particular solvent utilized, the amount of the polar solvent contained in a polymer blend used to form the drug-in-adhesive matrix layer can range from about 5 wt. % to about 30 wt. %, such as from about 10 wt. % to about 25 wt. %, such as from about 15 wt. % to about 20 wt. % based on the wet weight of the polymer blend. Meanwhile, after the polymer blend is coated onto, for instance, a backing layer and then dried to form the drug-in-adhesive matrix layer, the drug-in-adhesive matrix layer is generally free of the polar solvent.

d. Pressure Sensitive Adhesive

The drug-in-adhesive matrix layer of the transdermal drug delivery system of the present invention includes any suitable pressure sensitive adhesive (PSA). In one particular embodiment, the PSA is a solvated polyisobutylene-based PSA. The polyisobutylene-based PSA can have and a viscosity ranging from about 5000 mPa·s to about 8000 mPa·s, such as from about 5500 mPa·s to about 7500 mPa·s, such as from about 6000 mPa·s to about 7000 mPa·s, where the viscosity impacts the loading capacity of the components in polymer blend used to form the drug-in-adhesive matrix layer. One particular polyisobutylene-based PSA is commercially available under the name DuroTak® 87-6908, available from Henkel.

Regardless of the particular PSA utilized, the amount of the PSA contained in a polymer blend used to form the drug-in-adhesive matrix layer can range from about 15 wt. % to about 90 wt. %, such as from about 20 wt. % to about 85 wt. %, such as from about 40 wt. % to about 80 wt. % based on the wet weight of the polymer blend. Meanwhile, after the polymer blend is coated onto, for instance, a backing layer and then dried to form the drug-in-adhesive matrix layer, the pressure sensitive adhesive can be present in an amount ranging from about 20 wt. % to about 95 wt. %, such as from about 25 wt. % to about 90 wt. %, such as from about 45 wt. % to about 85 wt. % based on the dry weight of the drug-in-adhesive matrix layer after the transdermal drug delivery system is assembled and ready for use.

e. Plasticizer

The drug-in-adhesive matrix layer of the transdermal drug delivery system of the present invention can also include any suitable plasticizer. In one particular embodiment, the plasticizer can be an oil. Suitable oils that can be used as the plasticizer include mineral oils, plant-based oils, silicone oils, or a combination thereof. Examples of commercially available mineral oils, which are liquid petroleum derivatives that may be used in accordance with the present invention, can include Witco Corporation's Carnation® mineral oil or Penreco Corporation's Drakeol® mineral oil. Suitable plant-based oils, which are non-petroleum biomass derived oils, that can be used include vegetable or fruit oils, such as almond oil, peanut oil, wheat germ oil, linseed oil, jojoba oil, apricot pit oil, walnut oil, palm nut oil, pistachio nut oil, sesame seed oil, grapeseed oil, cade oil, corn oil, peach pit oil, poppy seed oil, pine oil, castor oil, soybean oil, avocado oil, safflower oil, coconut oil, hazelnut oil, olive oil, grape seed oil, sunflower oil, apricot kernel oil, geranium oil, rice bran oil and mixtures thereof. Silicone oils that can be used include disiloxane, dimethicone and derivatives thereof, and polydimethylsiloxane fluids.

Regardless of the particular solvent utilized, the amount of the plasticizer contained in a polymer blend used to form the drug-in-adhesive matrix layer can range from about 0.5 wt. % to about 12.5 wt. %, such as from about 0.75 wt. % to about 10 wt. %, such as from about 1 wt. % to about 7.5 wt. % based on the wet weight of the polymer blend. Meanwhile, after the polymer blend is coated onto, for instance, a backing layer and then dried to form the drug-in-adhesive matrix layer, the plasticizer can be present in an amount ranging from about 1 wt. % to about 25 wt. %, such as from about 2.5 wt. % to about 20 wt. %, such as from about 5 wt. % to about 15 wt. % based on the dry weight of the drug-in-adhesive matrix layer after the transdermal drug delivery system is assembled and ready for use.

f. Filler

The drug-in-adhesive matrix layer of the transdermal drug delivery system of the present invention also includes a filler that includes a mesoporous silica gel type of silicon dioxide having both internal and external porosity. The pores can have a diameter ranging from about 2 nanometer to about 50 nanometers, such as from about 2.5 nanometers to about 35 nanometers, such as from about 3 nanometers to about 20 nanometers. Meanwhile, the mesoporous silicon dioxide particles contemplated for use in the present invention can have a particle size ranging from about 1 micrometer to about 10 micrometers, such as from about 1.5 micrometers to about 9.5 micrometers, such as from about 2 micrometers to about 9 micrometers, which is larger than the particle size of fumed silica particles, which can, on average, have a 5 nanometer to 50 nanometer particle size, and colloidal silica particles, which can, on average, have a 2 nanometer to 100 nanometer particle size. Further, the average pore volume can range from about 0.2 $cm^3$/gram to about 2 $cm^3$/gram, such as from about 0.3 $cm^3$/gram to about 1.9 $cm^3$/gram, such as from about 0.4 $cm^3$/gram to about 1.8 $cm^3$/gram. As such, the silicon dioxide particles contemplated by the present invention can have an increased surface area compared to colloidal silicon dioxide and fumed silicon dioxide, both of which are generally non-porous. For example, the surface area of the mesoporous silicon dioxide particles can range from about 275 $m^2$/g to about 350 $m^2$/g, such as from about 280 $m^2$/g to about 325 $m^2$/g, such as from about 290 $m^2$/g to about 310 $m^2$/g. The mesoporous silicon dioxide particles can also have a generally neutral pH, such as from about 6 to about 8, such as from about 6 to about 7.5, such as from about 6 to about 7. Without intending to be limited by any particular theory, the present inventors have found that the generally neutral pH of the specific mesoporous silicon dioxide contemplated by the present invention in combination with the specific binder contemplated by the present invention can facilitate the controlled release of the API at a generally constant rate over a time period of up to about seven days without an excessively depleting delivery profile. Such a silicon dioxide is commercially available under the name Syloid® 72 FP from Grace/Mutchler. Other commercially available mesoporous silica gels that can be used include Syloid® 74 FP, 244 FP, and 266 FP, as well as Sipernat® silica gels from Evonik.

Regardless of the particular silicon dioxide filler utilized, the amount of the filler contained in a polymer blend used to form the drug-in-adhesive matrix layer can range from about 0.1 wt. % to about 10 wt. %, such as from about 0.25 wt. % to about 7.5 wt. %, such as from about 0.5 wt. % to about 5 wt. % based on the wet weight of the polymer blend. Meanwhile, after the polymer blend is coated onto, for instance, a backing layer and then dried to form the drug-in-adhesive matrix layer, the silicon dioxide filler can be present in an amount ranging from about 0.5 wt. % to about 15 wt. %, such as from about 0.75 wt. % to about 10 wt. %, such as from about 1 wt. % to about 5 wt. % based on the dry weight of the drug-in-adhesive matrix layer after the transdermal drug delivery system is assembled and ready for use. Further, the present inventors have found that specifically controlling the ratio of the specific filler (e.g., mesoporous silicon dioxide) to the specific binder (e.g., cross-linked PVP) can facilitate delivery of the API in a controlled manner without the delivery profile exhibiting the depletion phenomenon discussed above. In other words, the transdermal delivery system of the present invention can deliver the API to a patient at a generally constant rate for a time period of up to about 7 days. Specifically, the ratio of the silicon dioxide to the cross-linked PVP should range from about 1:1 to about 1:8, such as from about 1:1.1 to about 1:5, such as from about 1:1.25 to about 1:4, such as from about 1:1.5 to about 1:3.

g. Non-Polar Solvent

The polymer blend from which the drug-in-adhesive matrix layer of the transdermal drug delivery system of the present invention is formed can further include a non-polar solvent, which can be used to adjust the solids content of the pressure sensitive adhesive. In one particular embodiment, the non-polar solvent can be heptane. Regardless of the particular non-polar solvent utilized, the amount of the non-polar solvent contained in a polymer blend used to form the drug-in-adhesive matrix layer can range from about 2.5 wt. % to about 80 wt. %, such as from about 5 wt. % to about 70 wt. %, such as from about 10 wt. % to about 60 wt. % based on the wet weight of the drug-in-adhesive matrix layer as the components are first combined. Meanwhile, after the polymer blend is coated onto, for instance, a backing layer and then dried to form the drug-in-adhesive matrix layer, the drug-in-adhesive matrix layer is generally free of the non-polar solvent.

II. Backing Layer

Referring again to FIG. 1, in addition to the drug-in-adhesive matrix layer 110, the transdermal drug delivery system 100 of the present invention also includes a backing layer 120 that forms the exterior surface 140 of the transdermal drug delivery system 100. The backing layer 120 can have a moisture vapor transmission rate (MVTR) ranging from about 0.05 $g/m^2$/24 hours to about 10 $g/m^2$/24 hours, such as from about 0.1 $g/m^2$/24 hours to about 8 $g/m^2$/24 hours, such as from about 0.2 $g/m^2$/24 hours to about 6 $g/m^2$/24 hours. Although any suitable impervious backing layer can be utilized, in one particular embodiment of the present invention, the backing layer is a three-layer laminate that includes an outer-facing polyethylene layer, a middle aluminum vapor-coated polyester layer, and an inner facing ethylene vinyl acetate layer that is in contact with the drug-in-adhesive matrix layer 110. Such a backing layer is commercially available under the name Scotchpak® 9730 from 3M.

III. Release Liner

Referring still to FIG. 1, in addition to the drug-in-adhesive matrix layer 110 and the backing layer 120, the transdermal drug delivery system 100 of the present invention also includes a release liner 130 disposed on the skin-contacting surface 150 of the transdermal drug delivery system that protects the drug-in-adhesive matrix layer 110 of the transdermal drug delivery system 100 until it is ready to be applied to a patient's skin. Once the transdermal drug delivery system 100 is to be applied to a patient's skin at its skin-contacting surface 150, the release liner 130 can be removed and discarded. Although any suitable release liner can be utilized, in one particular embodiment of the present invention, the release liner is a fluoropolymer-based release liner. For instance, the release liner can be a fluorosilicone release liner. Such release liners are commercially available under the name SupraLiner® from Saint-Gobain.

IV. Method of Making the Transdermal Drug Delivery System

Figure 2:
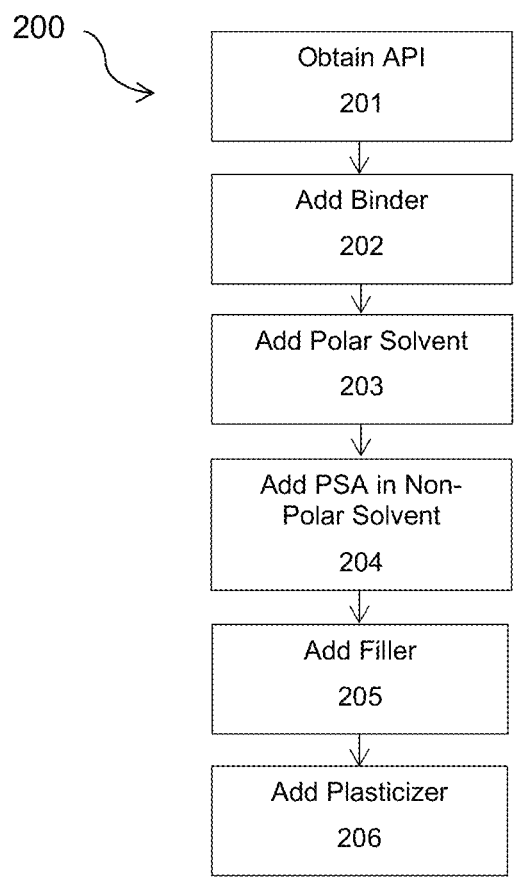
FIG. 2 is a flow chart illustrating a method of making the transdermal drug delivery system of FIG. 1.

Generally, the drug-in-adhesive matrix layer of the present invention is made by combining the components in a specific order, resulting in the ability to form a delivery system containing only one layer that utilizes an adhesive component, where such a layer also contains homogeneous dispersion of the API and forms the skin contacting surface of the delivery system once the release liner is removed. As such, the API can be delivered in a controlled manner over the course of up to about 7 days from a single layer. Referring to FIG. 2, one method 200 of making a polymer blend used to form the drug-in-adhesive matrix layer of the present invention is shown. First, in step 201, the API of interest is obtained (e.g., clonidine). Next, the binder is added to the API in step 202. Then, in step 203, the polar solvent is added. Next, in step 204, the pressure sensitive adhesive can be added, where the pressure sensitive adhesive can be solvated in the non-polar solvent. Thereafter, in step 205, the silicon dioxide filler can be added. Next, in step 206, the plasticizer can be added.

By forming the polymer blend in the manner discussed above, paying particular attention to the order of the addition of components as well as their weight percentages and ratios, the present inventors have found that the transdermal drug delivery system of the present invention, which includes only a single layer having an adhesive component in which the API is homogeneously distributed, can transdermally deliver an API in a uniform manner without the depletion phenomenon exhibited by known transdermal drug delivery systems that utilize a heterogeneous construction of multiple adhesive layers. In particular, the present inventors have found that the particular method 200 discussed above allows for complexing of the API with the binder, which is then uniformly distributed throughout the drug-in-adhesive matrix layer, where the binder and the ratio at which it is utilized with respect to the specific mesoporous silicon dioxide enables the formation of a uniform dispersion that facilitates non-depleting drug permeation from transdermal delivery patches for about a 7-day duration.

After the polymer blend used to form the drug-in-adhesive matrix layer 110 is coated onto a backing layer 120 and allowed to dry, a release liner 130 can be attached using any suitable method known by one of ordinary skill in the art. Depending on the specific requirements regarding drug delivery, the resulting transdermal drug delivery system or patch can have a skin-contacting surface area of from about 1 $cm^2$ to about 15 $cm^2$, such as from about 2 $cm^2$ to about 12.5 $cm^2$, such as from about 3 $cm^2$ to about 10 $cm^2$, such as when the API is clonidine. Further, the solids content of the drug-in-adhesive matrix layer of the transdermal drug delivery system can range from about 30% to about 40%, such as from about 31% to about 39%, such as from about 32% to about 38%. Further, the concentration of the API present in the transdermal drug delivery system of the present invention when the API is clonidine specifically can range from about 0.2 $mg/cm^2$ to about 1 $mg/cm^2$, such as from about 0.3 $mg/cm^2$ to about 0.9 $mg/cm^2$, such as from about 0.4 $mg/cm^2$ to about 0.8 $mg/cm^2$, such as from about 0.5 $mg/cm^2$ to about 0.7 $mg/cm^2$, while the coat weight of the drug-in-adhesive matrix layer in the transdermal drug delivery system can range from about 7 $mg/cm^2$ to about 10 $mg/cm^2$, such as from about 7.5 $mg/cm^2$ to about 9.5 $mg/cm^2$, such as from about 8 $mg/cm^2$ to about 9 $mg/cm^2$.

The present invention may be better understood by reference to the following examples.

COMPARATIVE EXAMPLE

First, the mean plasma clonidine concentration over time for a comparative sample that used an amorphous fumed silicon dioxide (Aerosil® 200) having an acidic pH between 3.7-4.5 as a filler instead of the neutral pH mesoporous silicon dioxide was compared to the commercially available product Catapres® as a reference or control. The specific components of the drug-in-adhesive matrix layer of the Comparative Example are shown below in Table 1.

TABLE 1

Drug-in-Adhesive Matrix Layer Components for Comparative Example
Drug-in-Adhesive Matrix Layer - Comparative Example

| Component | Dry Wt. % |
|---|---|
| Micronized Clonidine (API) | 6.0 |
| Cross-linked polyvinylpyrrolidone (Binder) | 5.0 |
| Polyisobutylene (Pressure Sensitive Adhesive) | 78.0 |
| Mineral Oil (Plasticizer) | 10.0 |
| Aerosil ® 200 Amorphous Fumed Silica (Filler) | 1.0 |
| Total | 100.00 |

Figure 3:
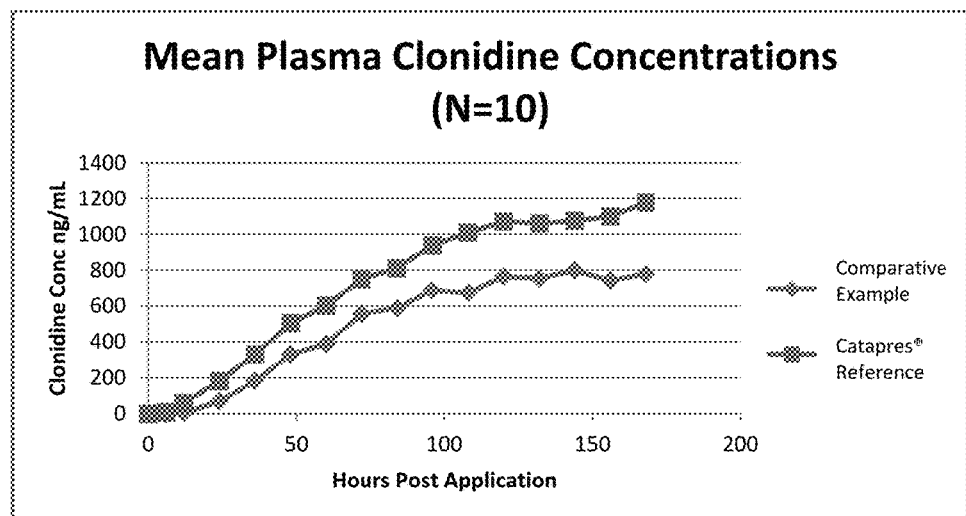
FIG. 3 is a graph illustrating the delivery of clonidine in humans (in terms of plasma concentration over time) from a transdermal drug delivery system as described in the Comparative Example that includes an acidic (pH 3.7-4.5) amorphous fumed silica (Aerosil®200) filler as compared to the commercially available Catapres® transdermal drug delivery system as the reference sample.

As shown in FIG. 3, the mean plasma concentration of clonidine delivered over a time period of about 160 hours was lower for the Comparative Example as compared to the Catapres® reference sample. Specifically, the maximum clonidine concentration for the Comparative Example was about 600 nanograms/m L, while the maximum clonidine concentration for the Catapres® reference sample was about 1200 nanograms/mL.

Example 1

Next, the mean plasma clonidine concentration over time for Example 1, which included a mesoporous silicon dioxide (Syloid® 72 FP) having a neutral pH between 6 and 7 as a filler instead of the acidic pH amorphous fumed silicon dioxide as in the Comparative Example was compared to the commercially available product Catapres® as a reference or control. The specific components of the drug-in-adhesive matrix layer of Example 1 are shown below in Table 2.

TABLE 2

Drug-in-Adhesive Matrix Layer Components for Example 1
Drug-in-Adhesive Matrix Layer - Example 1

| Component | Dry Wt. % |
|---|---|
| Micronized Clonidine (API) | 6.0 |
| Cross-linked polyvinylpyrrolidone (Binder) | 5.0 |
| Polyisobutylene (Pressure Sensitive Adhesive) | 77.0 |
| Mineral Oil (Plasticizer) | 10.0 |
| Mesoporous Silicon Dioxide (Filler) | 2.0 |
| Total | 100.00 |

Figure 4:
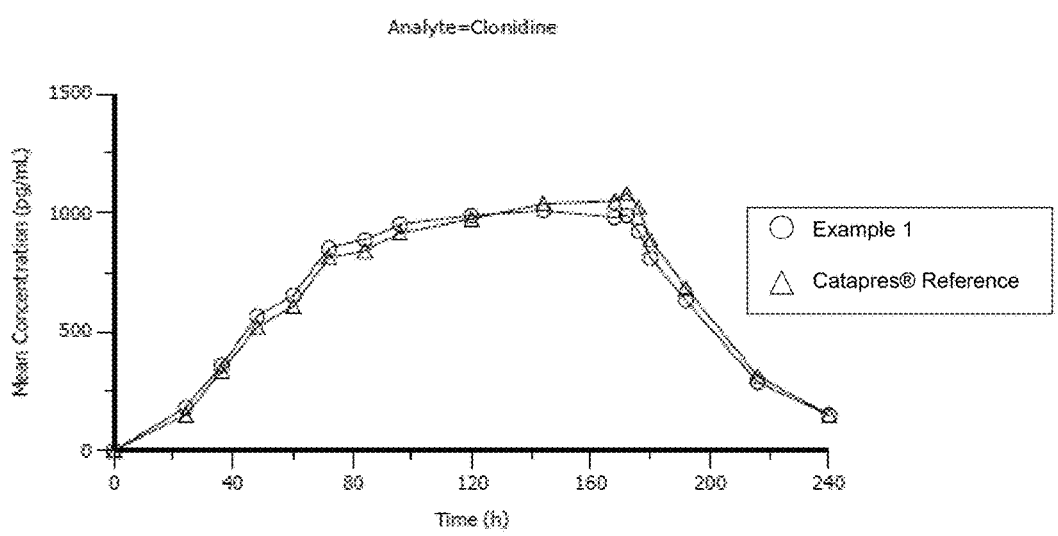
FIG. 4 is a graph illustrating the delivery of clonidine in humans (in terms of plasma concentration over time) from a transdermal drug delivery system of the present invention as described in Example 1 that includes a mesoporous silicon dioxide filler as compared to commercially available Catapres® transdermal drug delivery system as the reference sample.

As shown in FIG. 4, the mean plasma concentration of clonidine delivered over a time period of about 240 hours was generally the same for Example 1 and the Catapres® reference sample. Specifically, the maximum clonidine concentration for Example 1 was about 1100 nanograms/mL and the maximum clonidine concentration for the Catapres® reference sample was about 1100 nanograms/m L. This indicates that a similar drug delivery profile can be achieved for a transdermal drug delivery system that includes the monolithic drug-in-adhesive layer of Example 1, with a mesoporous silicon dioxide to cross-linked polyvinylpyrrolidone ratio of 1:2.5, and the commercial product which requires a drug reservoir, a control membrane, and a separate adhesive layer, where the system of the present invention is more efficient to manufacture and is less complex.

Example 2

Next, the ratio of mesoporous silicon dioxide to cross-linked polyvinylpyrrolidone in the drug-in-adhesive matrix of the present invention was varied between zero and 1:7.5 in samples A-D. The various weight percentages of the components in the drug-in-adhesive layers for samples A-D are shown below in Table 3.

TABLE 3

Drug-in-Adhesive Matrix Layer Components for Example 2
Drug-in-Adhesive Matrix Layer

| | Dry Wt. % | | | |
|---|---|---|---|---|
| Component | A | B | C | D |
| Micronized Clonidine (API) | 6 | 6 | 6 | 6 |
| Cross-linked polyvinylpyrrolidone (Binder) | 7.5 | 7.5 | 7.5 | 7.5 |
| Polyisobutylene (Pressure Sensitive Adhesive) | 76.5 | 75.5 | 74.5 | 72.5 |
| Mineral Oil (Plasticizer) | 10 | 10 | 10 | 10 |
| Mesoporous Silicon Dioxide (Filler) | 0 | 1 | 2 | 4 |
| Ratio of Mesoporous Silicon Dioxide to Cross-linked PVP | — | 1:7.5 | 1:3.75 | 1:1.875 |

Figure 5:
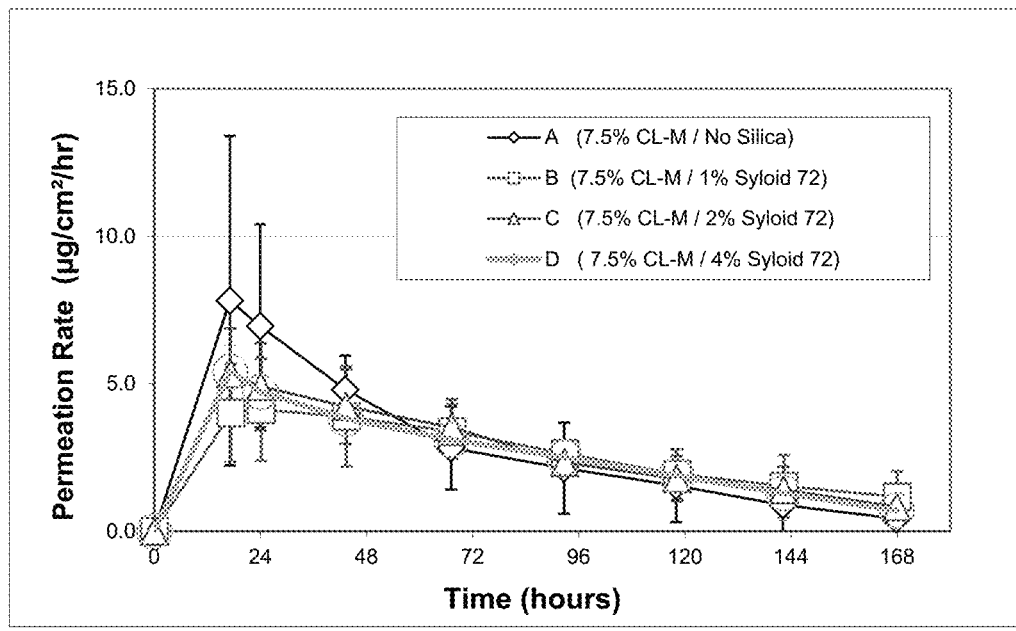
FIG. 5 is a graph illustrating the in vitro human cadaver skin permeation performance of the various drug-in-adhesive compositions A-D described in Example 2.

Samples A-D were tested for the permeation of clonidine through cadaver skin, where the permeation rate was measured in micrograms/cm²/hour. As shown in FIG. 5, the samples that included the mesoporous silicon dioxide (samples B-D) exhibited a more constant permeation rate over time compared to sample A, which did not include the mesoporous silicon dioxide and shows a high level of diffusion of the drug initially followed by a rapid decrease over time.

Example 3

Next, the ratio of mesoporous silicon dioxide to cross-linked polyvinylpyrrolidone in the drug-in-adhesive matrix of the present invention was varied between 1:1.875 and 1:3.75. The various weight percentages of the mesoporous silicon dioxide and polyvinylpyrrolidone components in the drug-in-adhesive layers for samples E-G are shown below in Table 4.

TABLE 4

Drug-in-Adhesive Matrix Layer Components for Example 3
Drug-in-Adhesive Matrix Layer

| | Dry Wt. % | | |
|---|---|---|---|
| Component | E | F | G |
| Micronized Clonidine (API) | 6 | 6 | 6 |
| Cross-linked polyvinylpyrrolidone (Binder) | 5 | 7.5 | 10 |
| Polyisobutylene (Pressure Sensitive Adhesive) | 77 | 74.5 | 72 |
| Mineral Oil (Plasticizer) | 10 | 10 | 10 |
| Mesoporous Silicon Dioxide (Filler) | 2 | 2 | 2 |
| Ratio of Mesoporous Silicon Dioxide to Cross-linked PVP | 1:2.5 | 1:3.75 | 1:5 |

Figure 6:
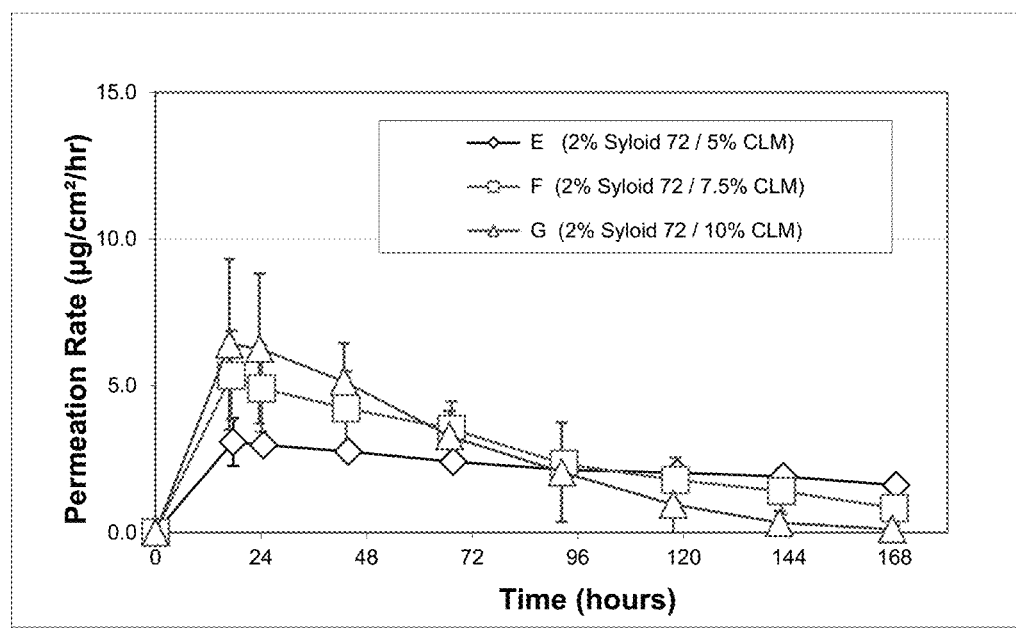
FIG. 6 is a graph illustrating the in vitro human cadaver skin permeation performance of three drug-in-adhesive compositions including 2 wt. % of mesoporous silicon dioxide particles (Syloid®) and varying amounts of cross-linked polyvinylpyrrolidone (Kollidon® CLM) binder described in Example 3.

Samples E-G were tested for the permeation of clonidine through cadaver skin, where the permeation rate was measured in micrograms/cm²/hour. As shown in FIG. 6, the lower the ratio of mesoporous silicon dioxide to cross-linked polyvinylpyrrolidone, the more constant the permeation rate over time (e.g., Sample E with a 1:2.5 mesoporous silicone dioxide to cross-linked polyvinylpyrrolidone ratio had a more constant permeation rate than Samples F and G). Thus, as shown from the above Examples, the mesoporous silicon dioxide having a neutral pH between 6 and 7 that is contemplated in the drug-in-adhesive layer of the transdermal drug delivery system of the present invention can remedy the problem seen in existing monolithic drug-in-adhesive layer, where the diffusion of the drug through the skin of the patient and into the bloodstream is often initially high and exhibits a rapid decrease over time so that the drug delivery is not controlled at the desired rate.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A transdermal drug delivery system comprising:
    a drug-in-adhesive matrix layer including an active pharmaceutical ingredient, a cross-linked polyvinylpyrrolidone binder, a mesoporous silicon dioxide filler, and a pressure sensitive adhesive; and
    a backing layer, wherein the backing layer forms an exterior facing-surface of the transdermal drug delivery system;
    wherein the ratio of the mesoporous silicon dioxide filler to the cross-linked polyvinylpyrrolidone binder ranges from 1 part mesoporous silicon dioxide filler to 1 part cross-lined polyvinylpyrrolidone binder up to 1 part mesoporous silicon dioxide filler to 8 parts cross-linked polyvinylpyrrolidone binder.

2. The transdermal drug delivery system of claim 1, wherein the mesoporous silicon dioxide filler has a pH ranging from about 6 to about 8.

3. The transdermal drug delivery system of claim 1, wherein the mesoporous silicon dioxide filler is in the form of particles having an average particle size ranging from about 1 micrometer to about 10 micrometers.

4. The transdermal drug delivery system of claim 3, wherein the mesoporous particles have an average pore size ranging from about 2 nanometers to about 50 nanometers.

5. The transdermal drug delivery system of claim 1, wherein the cross-linked polyvinylpyrrolidone binder is in the form of particles having an average particle size ranging from about 1 micrometer to about 40 micrometers.

6. The transdermal drug delivery system of claim 1, wherein the cross-linked polyvinylpyrrolidone binder is in the form of particles having a bulk density ranging from about 0.10 g/mL to about 0.25 g/mL.

7. The transdermal drug delivery system of claim 1, wherein the cross-linked polyvinylpyrrolidone binder is in the form of particles having a surface area ranging from about 0.5 $m^2$/g to about 20 $m^2$/g.

8. The transdermal drug delivery system of claim 1, wherein the pressure sensitive adhesive includes polyisobutylene.

9. The transdermal drug delivery system of claim 1, wherein the active pharmaceutical ingredient is clonidine.

10. The transdermal drug delivery system of claim 9, wherein the clonidine is present in the transdermal drug delivery system at a concentration ranging from about 0.2 mg/$cm^2$ to about 1 mg/$cm^2$.

11. The transdermal drug delivery system of claim 1, wherein the drug-in-adhesive matrix layer further includes an oil-based plasticizer.

12. The transdermal drug delivery system of claim 1, further comprising a release liner, wherein the release liner is disposed on a skin-contacting surface of the drug-in-adhesive matrix layer.

13. The transdermal drug delivery system of claim 1, wherein the active pharmaceutical ingredient is delivered to a patient at a constant rate for up to about 7 days.

14. The transdermal drug delivery system of claim 1, wherein the active pharmaceutical ingredient is homogeneously distributed throughout the drug-in-adhesive matrix layer, wherein the drug-in-adhesive matrix layer is the only adhesive-containing component in the transdermal drug delivery system.

15. A method of providing transdermal delivery of an active pharmaceutical ingredient to a patient for up to about seven days, the method comprising:
providing the transdermal delivery system according to claim 1,
affixing the transdermal delivery system to the patient; and
transdermally delivering the active pharmaceutical ingredient to the patient.

16. A method of making a drug-in-adhesive matrix layer for a transdermal drug delivery system, the method comprising:
providing an active pharmaceutical ingredient;
adding a cross-linked polyvinylpyrrolidone binder to the active pharmaceutical ingredient to form a blend;
adding a polar solvent to the blend;
adding a pressure sensitive adhesive dissolved in a non-polar solvent to the blend;
adding a plasticizer to the blend; and
adding a mesoporous silicon dioxide filler to the blend such that the ratio of the mesoporous silicon dioxide filler to the cross-linked polyvinylpyrrolidone binder ranges from 1 part mesoporous silicon dioxide filler to 1 part cross-linked polyvinylpyrrolidone binder up to 1 part mesoporous silicon dioxide filler to 8 parts cross-linked polyvinylpyrrolidone binder.

17. The method of claim 16, wherein the mesoporous silicon dioxide filler has a pH ranging from about 6 to about 8.

18. The method of claim 16, wherein the mesoporous silicon dioxide filler is in the form of particles having an average particle size ranging from about 1 micrometer to about 10 micrometers.

19. The method of claim 16, wherein the cross-linked polyvinylpyrrolidone binder is in the form of particles having an average particle size ranging from about 1 micrometer to about 40 micrometers.

20. The method of claim 16, wherein the polar solvent is ethyl acetate and the non-polar solvent is heptane.

* * * * *